United States Patent
Iwase

(10) Patent No.: US 7,800,747 B2
(45) Date of Patent: Sep. 21, 2010

(54) INSPECTION APPARATUS AND INSPECTION METHOD

(75) Inventor: Osamu Iwase, Kanagawa (JP)

(73) Assignee: NuFlare Technology, Inc., Numazu-shi (JP)

( * ) Notice: Subject to any disclaimer, the term of this patent is extended or adjusted under 35 U.S.C. 154(b) by 137 days.

(21) Appl. No.: 12/205,101

(22) Filed: Sep. 5, 2008

(65) Prior Publication Data

US 2009/0073430 A1 Mar. 19, 2009

(30) Foreign Application Priority Data

Sep. 19, 2007 (JP) ............................... 2007-242371

(51) Int. Cl.
*G01N 21/00* (2006.01)
(52) U.S. Cl. ................................. 356/237.1; 356/237.5
(58) Field of Classification Search ... 356/237.1–237.5, 356/239.1–239.8, 394
See application file for complete search history.

(56) References Cited

U.S. PATENT DOCUMENTS

| | | | |
|---|---|---|---|
| 2003/0086080 A1* | 5/2003 | Guan et al. | 356/237.1 |
| 2005/0190809 A1* | 9/2005 | Petersen et al. | 372/55 |
| 2007/0064223 A1* | 3/2007 | Imai | 356/237.1 |
| 2008/0013072 A1* | 1/2008 | Imai | 356/51 |
| 2009/0084989 A1* | 4/2009 | Imai | 250/492.22 |

FOREIGN PATENT DOCUMENTS

JP 2007-102153 4/2007

* cited by examiner

*Primary Examiner*—Hoa Q Pham
(74) *Attorney, Agent, or Firm*—Oblon, Spivak, McClelland, Maier & Neustadt, L.L.P.

(57) ABSTRACT

An inspection apparatus includes: a first light source having a first plurality of surface emitting laser elements which emit fundamental waves, respectively; a first illumination optical system configured to illuminate a first plurality of fundamental waves emitted from the first plurality of surface emitting laser elements on an object to be inspected; and a stage on which the object to be inspected is placed.

7 Claims, 8 Drawing Sheets

INSPECTION APPARATUS AND INSPECTION METHOD

CROSS-REFERENCE TO RELATED APPLICATION

This application is based upon and claims the benefit of priority from prior Japanese Patent Application No. 2007-242371 filed on Sep. 19, 2007 in Japan, the entire contents of which are incorporated herein by reference.

BACKGROUND OF THE INVENTION

1. Field of the Invention

The present invention relates to an inspection apparatus and an inspection method. For example, the present invention relates to an inspection apparatus and method which inspects a pattern formed on an object to be inspected.

2. Related Art

In recent years, with advance in high integration density and large capacity of a large-scale integrated circuit (LSI), a circuit line width required for a semiconductor element increasingly becomes narrow. These semiconductor elements are manufactured such that a pattern is exposed and transferred onto a wafer by using an original pattern (which is called a mask or a reticle and will be referred to as a mask hereinafter) on which a circuit pattern is formed, by means of a reduced projection exposure apparatus which is a so-called stepper to form a circuit. Therefore, in manufacturing of the mask to transfer such a micro-circuit pattern on a wafer, a pattern writing apparatus using an electron beam which can write a micro-circuit pattern is used. A pattern circuit may be directly written on a wafer by the pattern writing apparatus. Alternatively, a laser beam writing apparatus which writes a pattern by using a laser beam in place of an electron beam is attempted to be developed.

For manufacturing an LSI which is manufactured at a high cost, an increase in yield is necessary. However, as typified by a 1-Gbit-class DRAM (random access memory), the size of a pattern configuring an LSI changes from a sub-micron order to a nanometer order. As one of large factors which degrade an yield, a pattern defect of a mask used when ultra-micropattern is exposed and transferred on a semiconductor wafer by a photolithography technique is given. In recent years, with miniaturization of a size of an LSI pattern formed on a semiconductor wafer, a size to be detected as a pattern defect is also very small. For this reason, a pattern inspection apparatus which inspects a defect of a transfer mask used in manufacturing of an LSI requires to be increased in accuracy.

On the other hand, with advance in multimedia, in an LCD (Liquid Crystal Display), an increase in liquid crystal substrate size to 500 mm×600 mm or more and miniaturization of a pattern of a TFT (Thin Film Transistor) or the like formed on a liquid crystal substrate are advanced. Therefore, a very small pattern defect is required to be inspected in a wide area. For this reason, a pattern inspection apparatus which efficiently inspects a defect of a photomask used when patterns of a large-area LCD and a large-area LCD are manufactured within a short period of time must be urgently developed.

As an inspection method, a method of performing inspection by comparing an optical image obtained by picking an image of a pattern formed on a target object such as a lithography mask by using an magnifying optical system at a predetermined magnification, design data, or an optical image obtained by picking an image of the same pattern on the target object with each other is known. For example, as pattern inspection methods, "die to die inspection" which compares optical imaged at a obtained by picking images of the same patterns at different places on the same mask and "die to database inspection" which inputs write data (design pattern data) converted into an apparatus input format to be input by a writing apparatus into a inspection apparatus when a pattern is written by using pattern-designed CAD data as a mask, generates design image data (reference image) on the basis of the write data, and compares the design image data with an optical image serving as measurement data obtained by picking an image of the pattern are known. In the inspection method in the inspection apparatus, a target object is placed on a stage, and a beam scans the target object by movement of the stage to perform inspection. The target object is irradiated with a beam by a light source or an illumination optical system. The light passing through or reflected by the target object is focused on a sensor through an optical system. The images taken on the sensor are transmitted to a comparing circuit as measurement data. In the comparing circuit, after the images are aligned to each other, measurement data and reference data are compared with each other according to an appropriate algorithm. When the measurement data and the reference data are not matched with each other, the presence of a pattern defect is determined (for example, see Published Unexamined Japanese Patent Application No. 2007-102153 (JP-A-2007-102153)).

In a conventional pattern inspection apparatus, an optical image is acquired by using a continuous ultraviolet laser beam. As a light source which generates the ultraviolet laser beam, one large-scale light source such as an ion-laser light source or an excimer laser light source is arranged. Since a fundamental wave generated from the light source is coherent light, in the conventional pattern inspection apparatus, the coherent light is made incoherent through various optical devices. Although the light source itself is a large-scale device, furthermore, for example, various devices to make coherent light incoherent, such as a rotational phase plate and a tetrameric mirror must be arranged. For this reason, in the conventional pattern inspection apparatus, a very large space is disadvantageously necessary to install the pattern inspection apparatus.

As described above, in the conventional pattern inspection apparatus, a large-scale light source such as an ion laser or an excimer laser and various devices to make coherent light incoherent must be mounted. For this reason, the pattern inspection apparatus disadvantageously requires a very large space to install it. In addition, a conventional light source is expensive to increase the cost of the pattern inspection apparatus. Furthermore, various devices to make coherent light incoherent are a factor that increases the cost, as a matter of course.

BRIEF SUMMARY OF THE INVENTION

It is an object of the present invention to provide an inspection apparatus and method which can downsize a light source and omit a conventionally required device to make coherent light incoherent.

An inspection apparatus according to an embodiment of the present invention includes: a first light source having a first plurality of surface emitting laser elements which emit fundamental waves, respectively; a first illumination optical system configured to illuminate a first plurality of fundamental waves emitted from the first plurality of surface emitting laser elements on an object to be inspected; and a stage on which the object to be inspected is placed.

An inspection method according to an embodiment of the present invention includes emitting a plurality of fundamental waves from a plurality of surface emitting laser elements; and irradiating the plurality of fundamental waves emitted from the plurality of surface emitting laser elements on an object to be inspected on a stage.

DETAILED DESCRIPTION OF THE INVENTION

Embodiment 1

Figure 1:
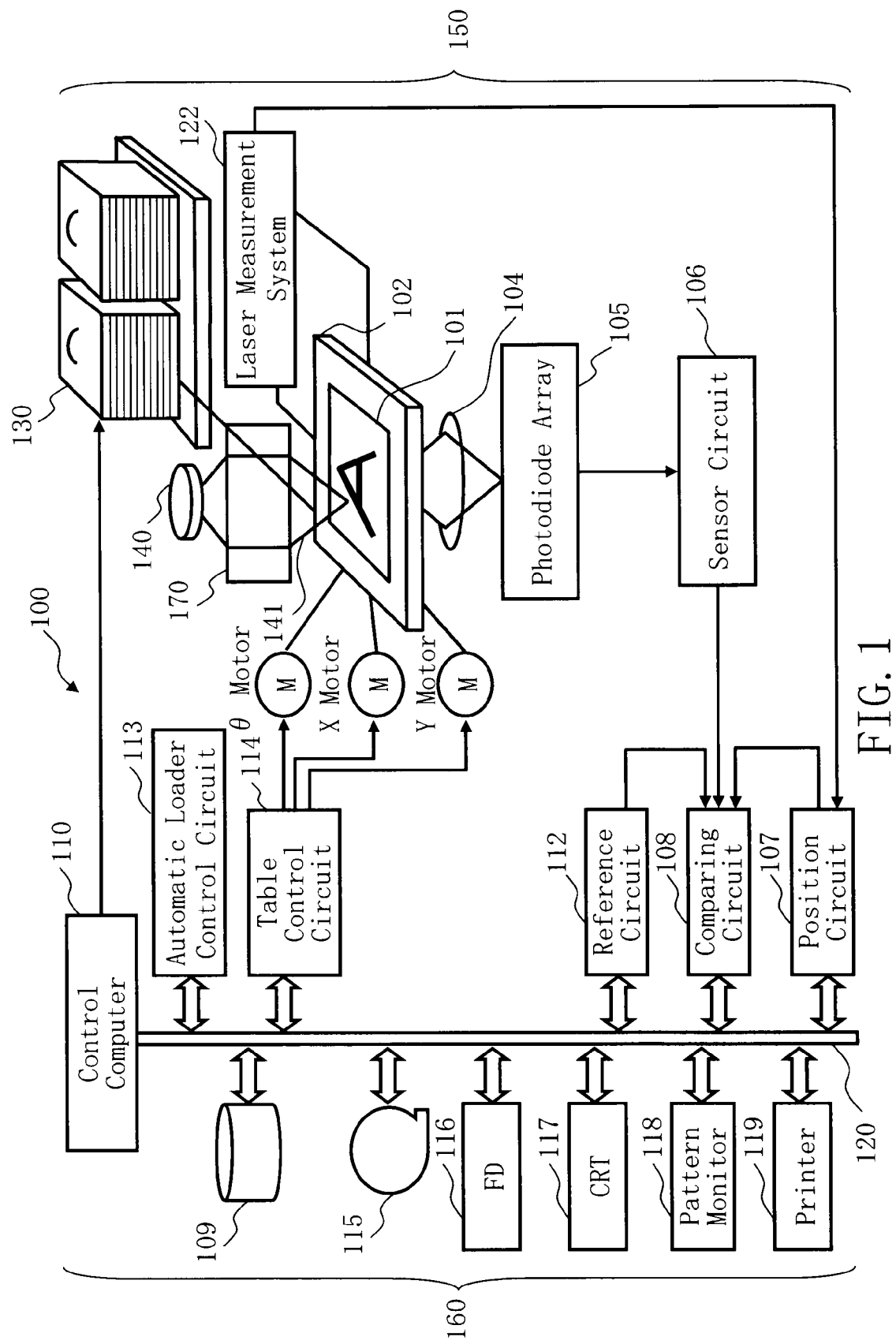
FIG. 1 is a conceptual diagram showing a configuration of a pattern inspection apparatus according to Embodiment 1.

FIG. 1 is a conceptual diagram showing a configuration of a pattern inspection apparatus according to Embodiment 1.

In FIG. 1, an inspection apparatus 100 which inspects a defect of a target object, for example, a mask includes an optical image acquiring unit 150 and a control system circuit 160. The optical image acquiring unit 150 includes a light source 140 having a plurality of surface emitting laser elements, an XYθ table 102, an illumination optical system 170 configuring a transparent illumination system, a magnifying optical system 104, a photodiode array 105 (photoelectric converting element, or "sensor"), a sensor circuit 106, a laser measurement system 122, and an automatic loader 130. In the control system circuit 160, a control computer 110 serving as a computer is connected to a position circuit 107, a comparing circuit 108 (comparing unit), a reference circuit 112, an automatic loader control circuit 113, a table control circuit 114, a magnetic disk device 109, a magnetic tape device 115, a flexible disk device (FD) 116, a CRT 117, a pattern monitor 118, and a printer 119 through a bus 120. The XYθ table 102 is driven by an X-axis motor, a Y-axis motor, and a θ-axis motor. The XYθ table 102 is an example of a stage. Here, in FIG. 1, constituent parts necessary to explain Embodiment 1 are described. In general, the inspection apparatus 100 may include other necessary components as a matter of course.

In the inspection apparatus 100, the light source 140, the XYθ table 102, the illumination optical system 170, the magnifying optical system 104, the photodiode array 105, and the sensor circuit 106 configure a high-power inspection optical system. The XYθ table 102 is driven by the table control circuit 114 under the control of the control computer 110. The XYθ table 102 can be moved by a drive system such as a three-axis (X-Y-θ) motor which drives the XYθ table 102 in an X direction, a Y direction, and a θ direction. As the X motor, the Y motor, and the θ motor, for example, step motors can be used. A moving position of the XYθ table 102 is measured by the laser measurement system 122 and supplied to the position circuit 107. A photomask 101 on the XYθ table 102 is automatically conveyed from the automatic loader 130 driven by the automatic loader control circuit 113 and automatically discharged after the inspection is finished.

The photomask 101 serving as a target object to be inspected is placed on the XYθ table 102 which can be moved in a horizontal direction or a rotating direction by the motors of the X, Y, and θ axes. The light source 140 which emits light substantially equivalent to incoherent light irradiates a continuous beam 141 on the pattern formed on the photomask 101 through the illumination optical system 170. The beam passing through the photomask 101 is focused on the photodiode array 105 as an optical image through the magnifying optical system 104, and is incident on the photodiode array 105.

Figure 2:
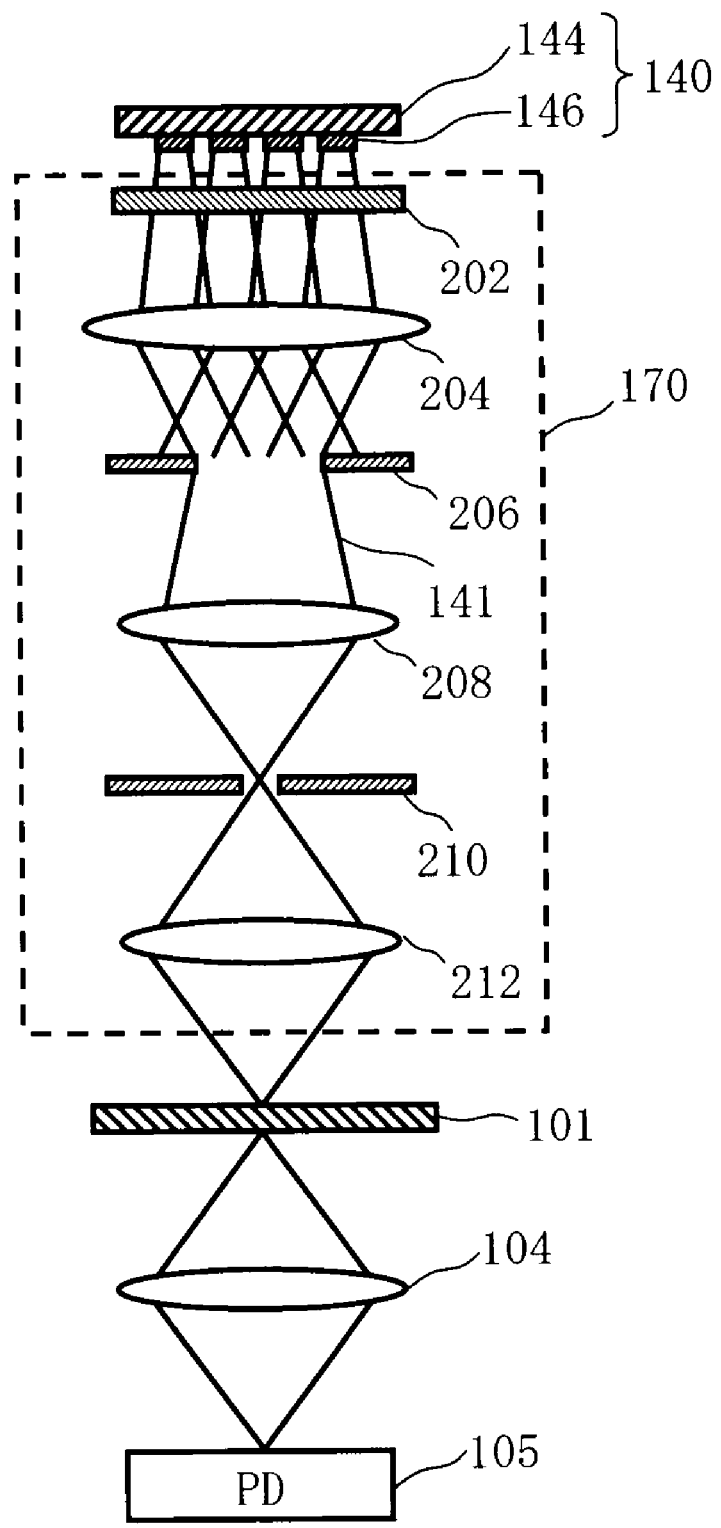
FIG. 2 is a conceptual diagram showing internal configurations of a light source and an illumination optical system according to Embodiment 1.

FIG. 2 is a conceptual diagram showing internal configurations of a light source and an illumination optical system according to Embodiment 1.

The light source 140 has a substrate 144 and a plurality of surface emitting laser elements 146 (first plurality of surface emitting laser elements) formed on the substrate 144. As the substrate 144, for example, an 8-inch silicon wafer can be used. The size of the silicon wafer is not limited to 8 inches, and may be 8 inches or more or 8 inches or less. More preferably, a silicon wafer having a size of less than 8 inches is preferably used. When film formation, patterning, and etching are repeated as in a semiconductor manufacturing process on the silicon wafer, so that the plurality of surface emitting laser elements 146 can be formed. The light source can be considerably made smaller than a large-scale light source device having meter-order width, depth, and height such as a conventional ion laser or an conventional excimer laser. At the same time, since an expensive light source is not necessary, cost of the light source can be suppressed. As a light-emitting step, each of the plurality of surface emitting laser elements 146 emits light as fundamental wave. For example, an element using indium gallium nitride (InGaN) can emit an ultraviolet ray having a wavelength of 380 to 400 nm as fundamental wave. Alternatively, for example, when InGaN is used, the shape of an InGaN crystal of the element is preferably changed to cause each of the surface emitting laser elements 146 to generate a second higher harmonic wave having a wavelength of 200 nm or less. A so-called inclined substrate in which a crystal axis is inclined unlike in a laser using a normal (100) crystal plane as a substrate to make it possible to generate the second higher harmonic wave.

In this case, on the substrate 144, for example, ten thousand or more surface emitting laser elements 146 are arranged. The number of arranged surface emitting laser elements 146 is not limited to this number. When the plurality of surface emitting laser elements 146 can be arranged, the number may be smaller than ten thousand. The number may be arbitrarily set on the basis of a desired amount of light and incoherent accuracy. The each of surface emitting laser elements 146 emits beams having almost equal amounts of light (light output). A plurality of fundamental waves (first plurality of fundamental waves) emitted from the plurality of surface emitting laser elements 146 at random without being subjected to phase adjustment are converged to be incoherent even though the each of fundamental waves are coherent light. Therefore, the fundamental waves are generated from the plurality of surface emitting laser elements 146 to make it possible to obtain substantially incoherent illumination light. Since the each of surface emitting laser elements 146 emits beams having almost equal amounts of light, the converged beam 141 can be uniformed.

For this reason, as the illumination optical system 170 (first illumination optical system), a configuration shown in FIG. 2 may be used. More specifically, the illumination optical system 170 includes an ND filter 202, a converging lens (first lens) 204, a field stop 206, a focusing lens 208 (second lens), an opening stop (σ) 210, and a condenser lens 212 (third lens). The ND filter 202, the converging lens 204, the field stop 206, the focusing lens 208, the σ stop 210, and the condenser lens 212 are sequentially arranged in an optical axis direction. For example, the focusing lens 208 and the condenser lens 212 are arranged in the optical axis direction to sandwich the σ stop 210. In the embodiment, the opening (σ) stop 210 is arranged on the downstream side of the field stop 206. However, this arrangement order is not limited to the order described above. The opening (σ) stop and the field stop may be relatively arranged in the order named. In Embodiment 1, since incoherent light can be obtained from the light source, for example, devices such as a rotating phase plate and a tetrameric mirror which are required to make the coherent light generated from a conventional single light source incoherent can be omitted. Furthermore, since the evenly uniform beam 141 can be obtained, devices such as an expander and an integrator lens can be omitted. Therefore, the apparatus can be made considerably compact. At the same time, since the cost of these devices is not necessary, the cost of the inspection apparatus can be suppressed. In the plurality of fundamental waves generated from the plurality of surface emitting laser elements 146, components in a predetermined wavelength region in the plurality of fundamental waves can be attenuated by the ND filter 202. The converging lens 204 converges the plurality of fundamental waves the components in the predetermined wavelength region of which are attenuated. The field stop 206 stops down the fields of the plurality of converged fundamental waves. Thereafter, the plurality of fundamental waves the fields of which are stopped down are focused on the σ stop 210 by the focusing lens 208, and the openings of the plurality of fundamental waves are stopped down by the σ stop 210. The continuous beam 141 passing through the σ stop 210 is focused on the photomask 101 serving as an object to be inspected by the condenser lens 212. In this manner, as the illuminating step, the plurality of fundamental waves emitted from the plurality of surface emitting laser elements 146 are irradiated on the photomask 101 on the XYθ table 102.

As described above, the light source 140 having the plurality of surface emitting laser elements 146 is mounted to make it possible to make the inspection apparatus considerably compact. Furthermore, the cost can be considerably suppressed.

Figure 3:
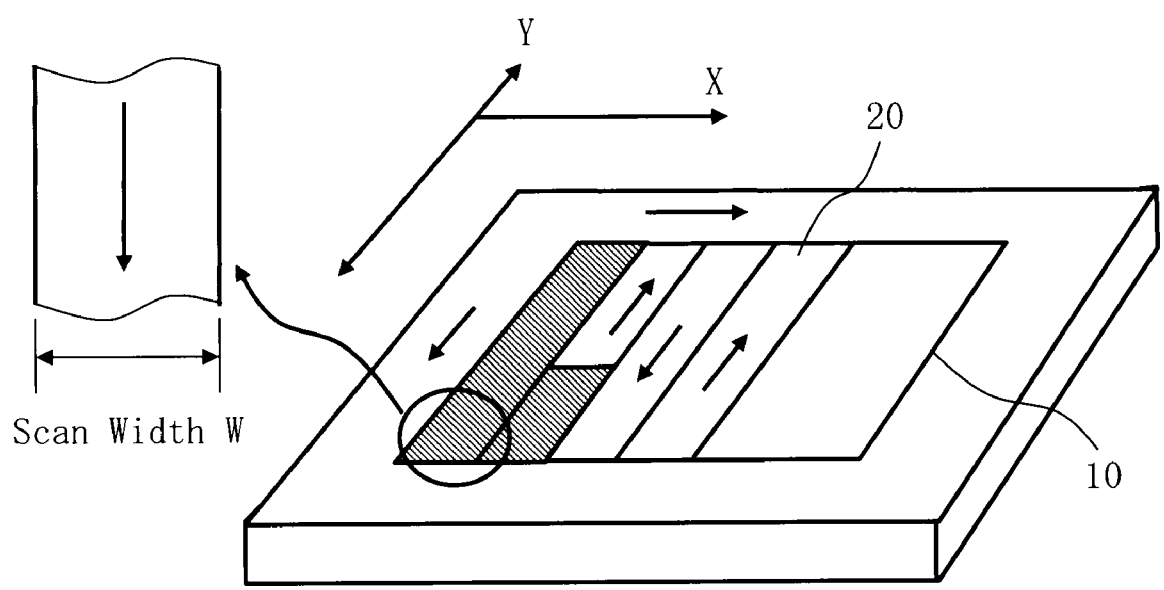
FIG. 3 is a conceptual diagram for explaining an acquiring procedure of an optical image according to Embodiment 1.

FIG. 3 is a conceptual diagram for explaining an acquiring procedure of an optical image according to Embodiment 1.

A region to be inspected 10, as shown in FIG. 3, is virtually divided into a plurality of inspection stripes 20 each having a scan width W in, for example, an X direction. The operation of the XYθ table 102 are controlled to continuously scan the divided inspection stripes 20. The optical image is acquired while relatively continuously moving the photodiode array 105 in a Y direction by moving the XYθ table 102. In the photodiode array 105, an optical image having the scan width W as shown in FIG. 3 is continuously picked. In Embodiment 1, after the optical image in one of the inspection stripes 20 is picked, in turn, the optical image having the scan width W can be similarly continuously picked while moving the XYθ table 102 in the reverse direction at a position shifted in the X direction by the scan width W. More specifically, an image pickup operation is repeated in a forward (FWD) direction to a backward (BWD) direction in opposite directions on a forward route and a backward route.

The continuous beam 141 passing through the photomask 101 is focused on the photodiode array 105 by the magnifying optical system 104. An image of a pattern focused on the photodiode array 105 is photoelectrically converted and further A/D (analog/digital)-converted by the sensor circuit 106. Thereafter, the each of pixel data of the photodiode array 105 are transmitted to the comparing circuit 108 together with data representing a position of the photomask 101 on the XYθ table 102 output from the position circuit 107. Measurement data is, for example, 8-bit sign less and expresses a grayscale of brightness (light amount) of each pixel.

When die-to-database inspection is to be performed, reference data (reference image) is formed by the reference circuit 112. More specifically, the reference circuit 112 reads design data from the magnetic disk device 109 through the control computer 110. The reference circuit 112 converts the design data of the photomask 101 into binary or many-valued image data to form reference data. The reference data is transmitted to the comparing circuit 108.

In the comparing circuit 108, alignment between the measurement data and the reference data is performed. The each of pixel data of the measurement data are compared with reference pixel data of the reference data according to a predetermined algorithm to determine the presence/absence of a defect. The comparison result is output. The comparison result is output to, for example, the magnetic disk device 109, the magnetic tape device 115, the FD 116, the CRT 117, the pattern monitor 118, or the printer 119. Alternatively, the result may be output to the outside.

On the other hand, die-to-die inspection is performed as follows. The measurement data (reference image) of a reference target object the image of which is picked together with the image of the target object to be inspected is transmitted to the comparing circuit 108 together with data representing the position of the photomask 101 on the XYθ table 102 output from the position circuit 107. In the comparing circuit 108, alignment between the measurement data and the reference data is performed first. The each of pixel data of the measurement data and the reference pixel data of the reference data are compared with each other according to a predetermined algorithm to determine the presence/absence of a defect. The comparison result is output. The comparison result is output to, for example, the magnetic disk device 109, the magnetic tape device 115, the FD 116, the CRT 117, the pattern monitor 118, or the printer 119. Alternatively, the comparison result may be output to the outside.

As described above, the light source 140 having the plurality of surface emitting laser elements 146 is arranged to make it possible to omit a device to make to obtain incoherent light. Furthermore, uniform light can be obtained without a device such as an integrator. As a result, the inspection apparatus can be made considerably compact. At the same time, the manufacturing cost of the inspection apparatus can be considerably reduced. In addition, a manufacturing period can be shortened, and maintenance can be simplified.

Embodiment 2

In Embodiment 1, the configuration using the transparent illumination system is described. However, another configuration may be employed. In Embodiment 2, a configuration using a reflecting illumination system will be described below.

Figure 4:
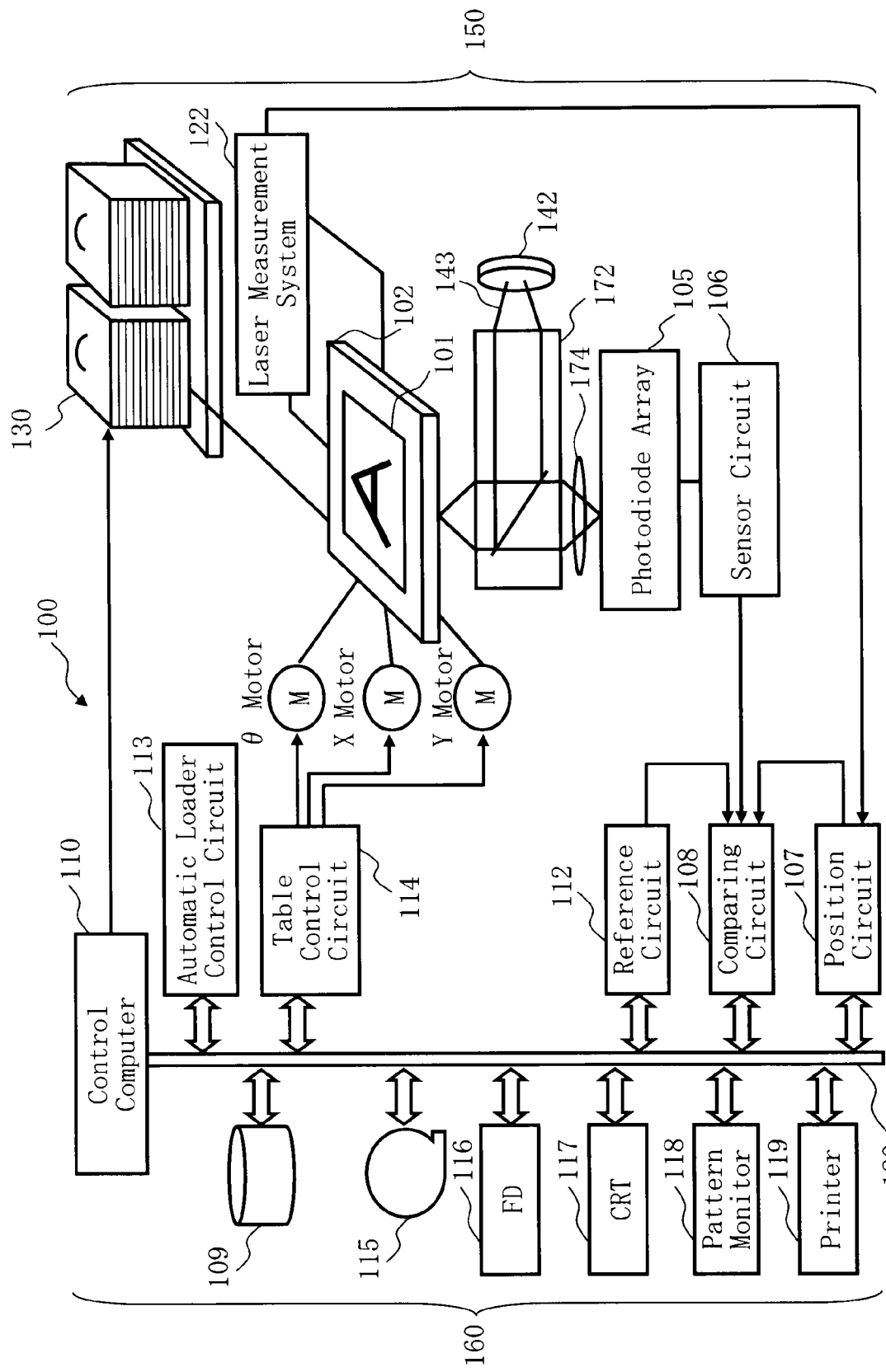
FIG. 4 is a conceptual diagram showing a configuration of a pattern inspection apparatus according to Embodiment 2.

FIG. 4 is a conceptual diagram showing a configuration of a pattern inspection apparatus according to Embodiment 2.

The configuration in FIG. 4 is the same as that in FIG. 1 except that an illumination optical system 172 (first or second illumination optical system) configuring a reflecting illumination system is arranged in place of the illumination optical system 170 configuring the transparent illumination system, a light source 142 having a plurality of surface emitting laser elements like the light source 140 is arranged in place of the light source 140 to be aligned to an optical axis direction of the illumination optical system 172, and a focusing lens 174 is arranged in place of the magnifying optical system 104. Here, in FIG. 4, constituent parts necessary to explain Embodiment 2 are described. In general, the inspection apparatus 100 may include other necessary components as a matter of course.

In the inspection apparatus 100, the light source 142, the XYθ table 102, the illumination optical system 172, the focusing lens 174, the photodiode array 105, and the sensor circuit 106 configure a high-power inspection optical system.

Figure 5:
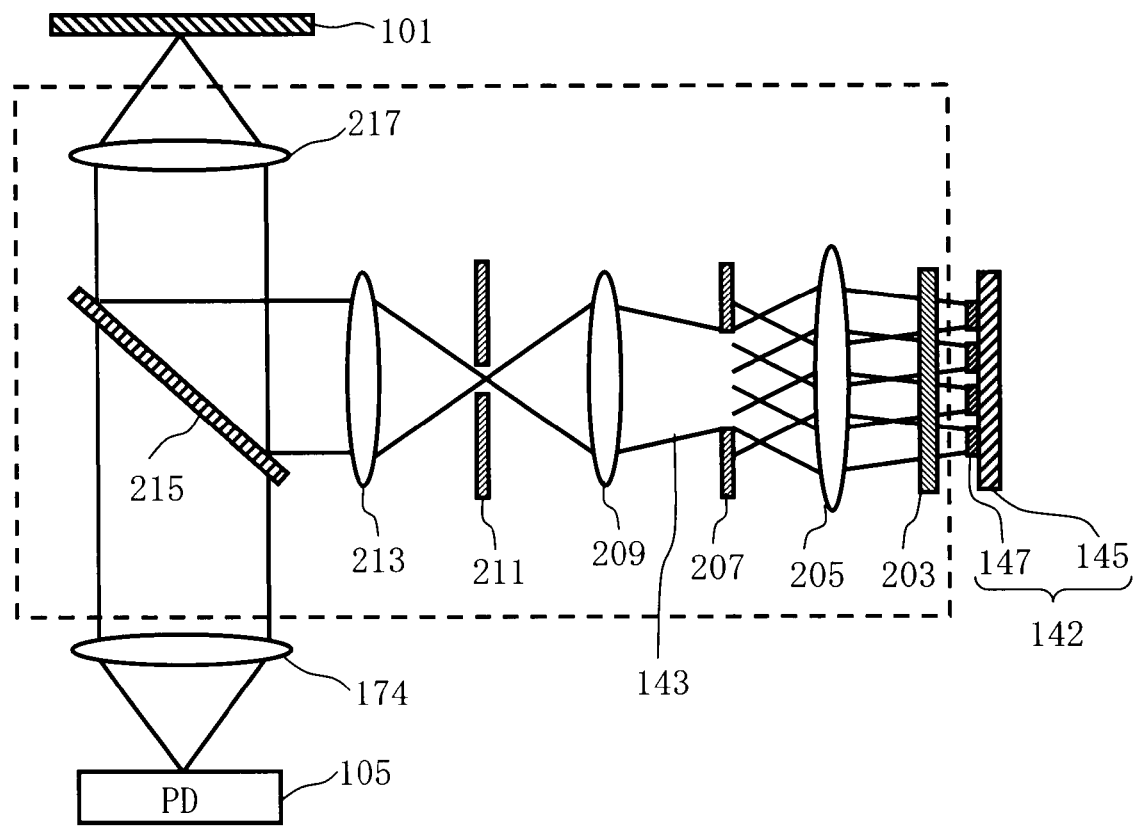
FIG. 5 is a conceptual diagram showing internal configurations of a light source and an illumination optical system according to Embodiment 2.

FIG. 5 is a conceptual diagram showing internal configurations of a light source and an illumination optical system according to Embodiment 2.

The light source 142 has a substrate 145 and a plurality of surface emitting laser elements 147 (first or second plurality of surface emitting laser elements) formed on the substrate 145. As the substrate 145, like the substrate 144, for example, an 8-inch silicon wafer can be used. The size of the silicon wafer is not limited to 8 inches, and may be 8 inches or more or 8 inches or less. More preferably, a silicon wafer having a size of less than 8 inches is preferably used. When film formation, patterning, and etching are repeated as in a semiconductor manufacturing process on the silicon wafer, so that the surface emitting laser elements 147 can be formed. The light source 142 is the same as the light source 140 except for an arrangement direction. Therefore, here, for example, an element using InGaN can emit an ultraviolet ray having a wavelength of 380 to 400 nm as fundamental wave. Alternatively, for example, when the shape of an InGaN crystal of the element is preferably changed to cause each of the surface emitting laser elements to generate a second higher harmonic wave having a wavelength of 200 nm or less.

In this case, on the substrate 145, for example, ten thousand or more surface emitting laser elements 147 are also arranged. The each of surface emitting laser elements 147 emit beams having almost equal amounts of light (light output). A plurality of fundamental waves (first or second plurality of fundamental waves) emitted from the plurality of surface emitting laser elements 147 at random without being subjected to phase adjustment are converged to be incoherent even though the fundamental waves are coherent light. Therefore, substantially incoherent illumination light also can be obtained. Since the each of surface emitting laser elements 147 emit beams having almost equal amounts of light, the converged beam 143 can be uniformed.

For this reason, when the reflecting illumination system is used, as the illumination optical system 172, a configuration shown in FIG. 5 may be used. More specifically, the illumination optical system 172 includes an ND filter 203, a condenser lens 205 (first lens), a field stop 207, a focusing lens 209 (second lens), an opening (σ) stop 211, a condenser lens 213 (third lens), half mirror 215 and objective lens 217. The configuration in FIG. 2 is the same as that of the illumination optical system 170 except that the half mirror 215 and the objective lens 217 are added. The ND filter 203, the condenser lens 205, the field stop 207, the focusing lens 209, the σ stop 211, the condenser lens 213, and the half mirror 215 are sequentially arranged in the horizontal optical axis direction. For example, the focusing lens 209 and the condenser lens 213 are arranged in the optical axis direction to sandwich the σ stop 211. In the embodiment, the opening (σ) stop 211 is arranged on the downstream side of the field stop 207. However, this arrangement order is not limited to the order described above. The opening (σ) stop and the field stop may be relatively arranged in the order named. In Embodiment 2, since incoherent light can be obtained from the light source 142, for example, devices such as a rotating phase plate and a tetrameric mirror which are required to make the coherent light generated from a conventional single light source incoherent can be omitted. Furthermore, since the evenly uniform beam 143 can be obtained, devices such as an expander and an integrator lens can be omitted. Therefore, the apparatus can be made considerably compact. At the same time, since the cost of these devices are not necessary, the cost of the inspection apparatus can be suppressed. The plurality of fundamental waves generated from the plurality of surface emitting laser elements 147, as in Embodiment 1, can be irradiated on the half mirror 215 through the ND filter 203, the condenser lens 205, the field stop 207, the focusing lens 209, the σ stop 211, and the condenser lens 213. The optical axis directions of the plurality of fundamental waves are deflected at 90° by the half mirror 215. The fundamental waves are directed to the photomask 101 serving as an object to be inspected. The beam 143 reflected by the half mirror 215 is focused on a rear surface of the photomask 101 serving as an object to be inspected by the objective lens 217. In this manner, as the irradiating step, the plurality of fundamental waves emitted from the plurality of surface emitting laser elements 146 are irradiated on the photomask 101 on the XYθ table 102. The beam 143 reflected by the photomask 101 passes through the objective lens 217 and the half mirror 215, and are focused on the photodiode array 105 by the focusing lens 174. The subsequent operation is the same as that in Embodiment 1.

As described above, the light source 142 having the plurality of surface emitting laser elements 147 is mounted to make it possible to omit a device to make coherent light incoherent even in the reflecting illumination system. Similarly, an evenly uniform light can be obtained without using a device such as an integrator. Therefore, the apparatus can be made considerably compact. At the same time, the manufacturing cost of the inspection apparatus can be considerably reduced.

Embodiment 3

The configuration using the transparent illumination system is described in Embodiment 1, and the configuration using the reflecting illumination system is described in Embodiment 2. However, other configurations may be used. In Embodiment 3, two illumination systems including a transparent illumination system and a reflecting illumination system will be described.

Figure 6:
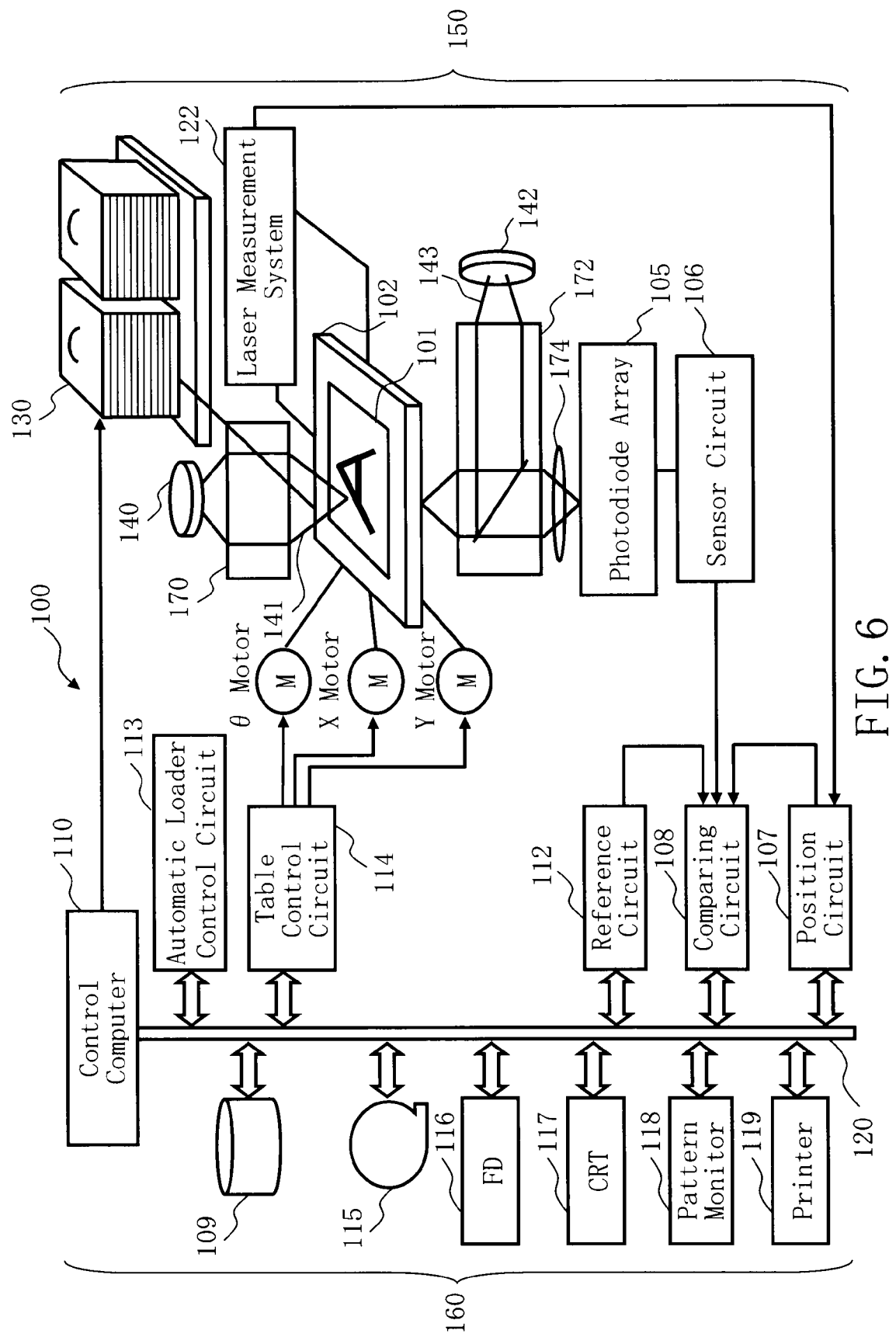
FIG. 6 is a conceptual diagram showing a configuration of a pattern inspection apparatus according to Embodiment 3.

FIG. 6 is a conceptual diagram showing a configuration of a pattern inspection apparatus according to Embodiment 3.

The configuration in FIG. 6 is the same as that in FIG. 1 except that the illumination optical system 172 (second illumination optical system) configuring a reflecting illumination system is arranged in addition to the illumination optical system 170 configuring a transparent illumination system, that the light source 142 (second light source) for the reflecting illumination system is arranged in addition to the light source 140 for the transparent illumination system, and that the focusing lens 174 is arranged in place of the magnifying optical system 104. Here, in FIG. 6, constituent parts necessary to explain Embodiment 3 are described. In general, the inspection apparatus 100 may include other necessary components as a matter of course.

Figure 7:
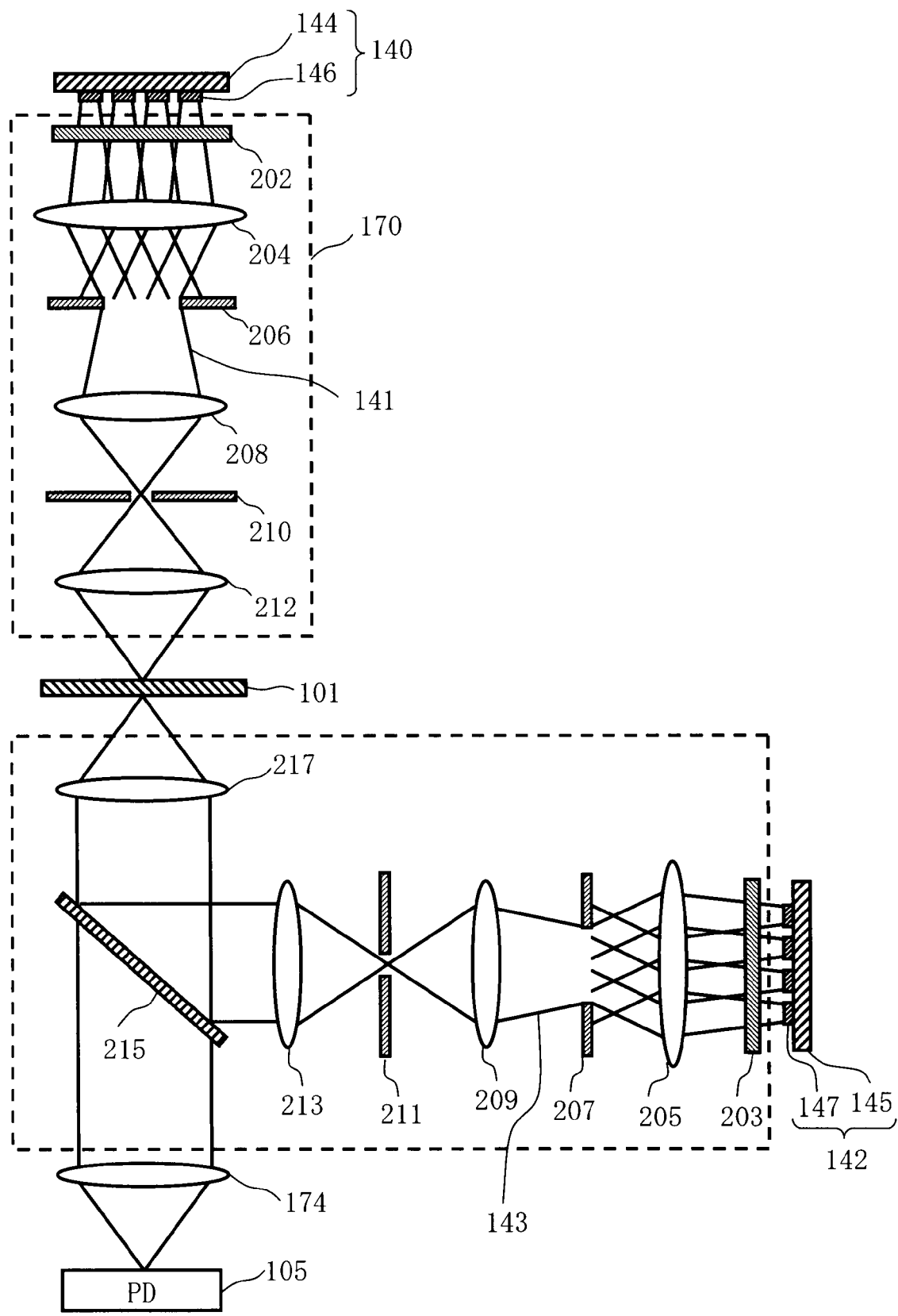
FIG. 7 is a conceptual diagram showing internal configurations of a light source and an illumination optical system according to Embodiment 3.

FIG. 7 is a conceptual diagram showing internal configurations of a light source and an illumination optical system according to Embodiment 3.

In FIG. 7, in addition to the configuration including the light source 140 and the illumination optical system 170 of the transparent illumination system shown in FIG. 2, the configuration including the light source 142 and the illumination optical system 172 of the reflecting illumination system shown in FIG. 5 is arranged. More specifically, the plurality of surface emitting laser elements 146 of the first light source 140 emit fundamental waves, respectively. The first illumination optical system 170 irradiates a first plurality of fundamental waves emitted from the first plurality of surface emitting laser elements 146 on the photomask 101 serving as an object to be inspected. An image of a pattern obtained by causing the fundamental waves to pass through the photomask 101 is inspected. Fundamental waves are also emitted from the second plurality of surface emitting laser elements 147 of the second light source 142, respectively. The second illumination optical system 172 reflects the second plurality of fundamental waves emitted from the second plurality of surface emitting laser elements 147 to irradiate the second fundamental waves on the photomask 101 serving as an object to be inspected. The image of the pattern obtained by reflecting the fundamental waves by the photomask 101 is inspected. In this manner, both the image obtained by causing the fundamental waves to pass through the photomask 101 and the image obtained by reflecting the fundamental waves by the photomask 101 can be inspected. Therefore, inspection accuracy can be improved.

Two large-scale light source apparatuses such as a light source, for example, a conventional ion laser or a conventional excimer laser having one or more meter in width, depth, and height are difficult to be installed for transmission or reflection. Conventional light source apparatus is expensive and it is difficult to install two large-scale light source apparatuses for transmission or reflection. As a result, illumination light generated from one of the light source apparatuses is branched for transmission and reflection. For this reason, disadvantageously, the amounts of light are ½ each. In contrast to this, in Embodiment 3, for example, since illumination lights are generated from the plurality of surface emitting laser elements 146 arranged on the small 8-inch substrate 144, a considerably compact inspection apparatus can be obtained at a low cost. For this reason, even though the light is not branched, two light sources 140 and 142 can be mounted. Since the two light sources are mounted, an optical system for branching can be omitted. For this reason, an apparatus configuration can be simplified. Therefore, furthermore, a compact apparatus can be achieved. Other configurations and operations are the same as those in Embodiments 1 and 2.

Embodiment 4

In each of the embodiments, fundamental waves generated from the plurality of surface emitting laser elements are directly used. However, other fundamental waves may be used.

Figure 8:
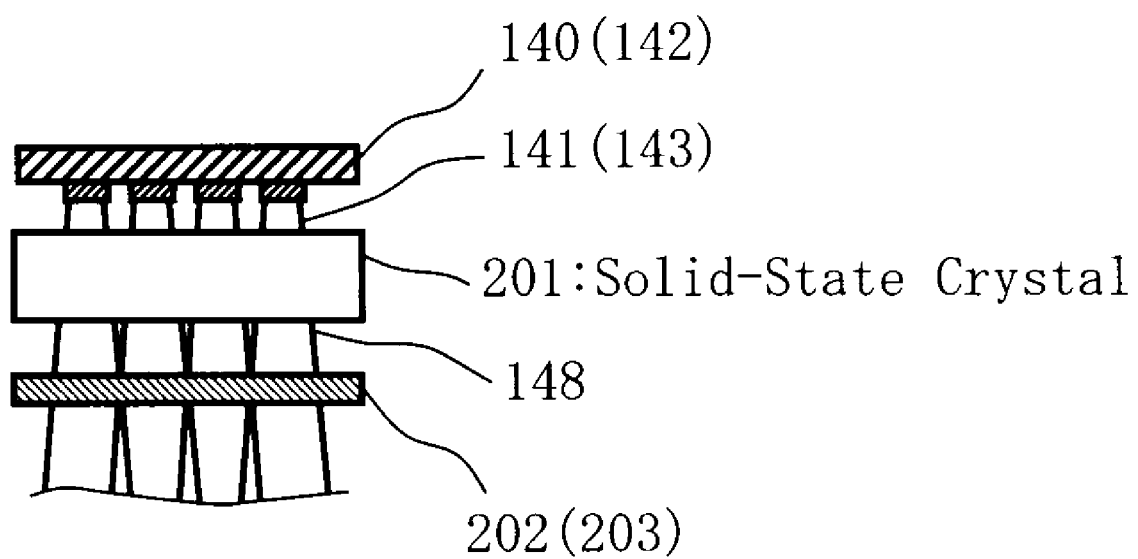
FIG. 8 is a conceptual diagram showing a configuration which generates a second higher harmonic wave in Embodiment 4.

FIG. 8 is a conceptual diagram showing a configuration which generates a second higher harmonic wave in Embodiment 4.

In FIG. 8, a solid-state nonlinear crystal 201 is arranged between the light source 140 (or the light source 142) and the ND filter 202 (or the ND filter 203). The solid-state nonlinear crystal 201 input a plurality of fundamental waves emitted from a plurality of surface emitting laser elements 146 (or a plurality of surface emitting laser elements 147) to generate second higher harmonic waves serving as a plurality of fundamental waves. For example, InGaN is used in the plurality of surface emitting laser elements 146 (or the plurality of surface emitting laser elements 147), a second higher harmonic wave 148 having a wavelength of 200 nm or less can be generated from the beam 141 (or the beam 143) having a wavelength of 380 to 400 nm. As the solid-state nonlinear crystal 201, for example, BBO ($\beta$-$BaB_2O_4$) or CLBO ($CsLiB_6O_{10}$) are preferably used. Other configurations and operations are the same as those in at least one of the embodiments.

The embodiments are described with reference to the specific examples. However, the present invention is not limited to the specific examples.

Parts such as an apparatus configuration and a control method which are not directly necessary for the explanation of the present invention are omitted. However, a necessary apparatus configuration and a necessary control method can be arbitrarily selected and used. For example, a description of a control unit configuration for controlling the inspection apparatus 100 is omitted. However, a necessary control unit configuration can be arbitrarily selected and used, as a matter of course.

Furthermore, all light sources, illumination optical systems, pattern inspection apparatuses, and pattern inspection methods which fulfill the components of the present invention and can be arbitrary changed in design by a person skilled in the art are included in the scope of the present invention.

Additional advantages and modification will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An inspection apparatus comprising:
a first light source including a first plurality of surface emitting laser elements which emit fundamental waves, respectively;
a first illumination optical system configured to illuminate a first plurality of fundamental waves emitted from the first plurality of surface emitting laser elements on an object to be inspected; and
a stage on which the object to be inspected is placed,
wherein the first illumination optical system includes:
a filter configured to attenuate a component in a predetermined wavelength region in the first plurality of fundamental waves;
a first lens configured to converge the first plurality of fundamental waves components in the predetermined wavelength region of which are attenuated;
a field stop configured to stop down a field of the first plurality of fundamental waves;
an opening stop configured to stop down an opening of the first plurality of fundamental waves; and
second and third lenses arranged in an optical axis direction to sandwich the opening stop.

2. The apparatus according to claim 1, further comprising:
a photoelectric converting element configured to receive the first plurality of fundamental waves passing through the object to photoelectrically convert the first plurality of fundamental waves; and
a comparing unit configured to compare output data of the photoelectric converting element with reference data.

3. The apparatus according to claim 1, further comprising:
a photoelectric converting element configured to receive the first plurality of fundamental waves reflected by the object to photoelectrically convert the first plurality of fundamental waves; and
a comparing unit configured to compare output data of the photoelectric converting element with reference data.

4. The apparatus according to claim 1, further comprising:
a nonlinear crystal configured to input the first plurality of fundamental waves emitted from the plurality of first surface emitting laser elements to generate second higher harmonic waves of the first plurality of fundamental waves.

5. The apparatus according to claim 1, wherein the first illumination optical system configures a transparent illumination system, further comprising:
a second light source including a second plurality of surface emitting laser elements which emit fundamental waves, respectively; and
a second illumination optical system configured to reflect a second plurality of fundamental waves emitted from the second plurality of surface emitting laser elements to irradiate the second plurality of fundamental waves on the object.

6. The apparatus according to claim 5, wherein the second illumination optical system includes:
a filter configured to attenuate components in a predetermined wavelength region in the second plurality of fundamental waves;
a first lens configured to converge the second plurality of fundamental waves the components in the predetermined wavelength region of which are attenuated;
a field stop configured to stop down a field of the second plurality of fundamental waves;
an opening stop configured to stop down an opening of the second plurality of fundamental waves; and
second and third lenses arranged in an optical axis direction to sandwich the opening stop.

7. The apparatus according to claim 6, further comprising:
a nonlinear crystal configured to input the second plurality of fundamental waves emitted from the second plurality of surface emitting laser elements to generate second higher harmonic waves of the second plurality of fundamental waves.

* * * * *